(12) United States Patent
Voth et al.

(10) Patent No.: US 10,049,771 B2
(45) Date of Patent: Aug. 14, 2018

(54) LAPLACIAN AND TIKHONOV REGULARIZATION FOR VOLTAGE MAPPING WITH A MEDICAL DEVICE

(71) Applicant: St. Jude Medical, Atrial Fibrillation Division, Inc., St. Paul, MN (US)

(72) Inventors: Eric Jon Voth, Maplewood, MN (US); D. Curtis Deno, Andover, MN (US); Lev Abramovich Koyrakh, Plymouth, MN (US); Braden Eliason, Shoreview, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 311 days.

(21) Appl. No.: 13/839,074

(22) Filed: Mar. 15, 2013

(65) Prior Publication Data

US 2014/0278129 A1 Sep. 18, 2014

(51) Int. Cl.
*G16H 50/50* (2018.01)
*A61B 5/0402* (2006.01)
*A61B 5/042* (2006.01)

(52) U.S. Cl.
CPC .......... *G16H 50/50* (2018.01); *A61B 5/0402* (2013.01); *A61B 5/0422* (2013.01)

(58) Field of Classification Search
None
See application file for complete search history.

(56) References Cited

U.S. PATENT DOCUMENTS

| | | | |
|---|---|---|---|
| 5,483,968 A | 1/1996 | Adam et al. | |
| 6,915,166 B1 * | 7/2005 | Stecker ............. | A61N 1/36032 607/45 |
| 7,263,397 B2 | 8/2007 | Hauck et al. | |
| 8,317,744 B2 | 11/2012 | Kirschenman | |
| 8,317,745 B2 | 11/2012 | Kirschenman et al. | |
| 2003/0120163 A1 | 6/2003 | Rudy et al. | |
| 2007/0060833 A1 | 3/2007 | Hauck | |
| 2007/0299353 A1 | 12/2007 | Harlev et al. | |
| 2009/0177072 A1 | 7/2009 | Harlev et al. | |
| 2009/0247943 A1 | 10/2009 | Kirschenman | |
| 2009/0247993 A1 | 10/2009 | Kirschenman | |
| 2010/0073150 A1 | 3/2010 | Olson et al. | |
| 2011/0275949 A1 | 11/2011 | Harlev et al. | |
| 2012/0035459 A1 | 2/2012 | Shotaevic et al. | |
| 2012/0172702 A1 | 7/2012 | Koyrakh et al. | |

FOREIGN PATENT DOCUMENTS

| | | |
|---|---|---|
| CN | 101002674 | 7/2007 |
| CN | 101283908 | 10/2008 |
| CN | 102958429 | 3/2013 |
| EP | 2436309 | 4/2012 |
| JP | H06-187426 | 7/1994 |
| JP | 2008068084 | 3/2008 |
| JP | 2008142154 | 6/2008 |
| WO | 2007/146864 | 12/2007 |

OTHER PUBLICATIONS

Fischer, "Application of high-order boundary elements to the electrocardiographic inverse problem," Computer methods and programs in biomedicine, vol. 58, p. 119-131, 1999.*
Lunttila, "Regularization in Cardiac Source Imaging," in Functional Imaging and Modeling of the Heart, Springer, Berlin, p. 101-110, 2003.*
Cottereau, "Multiresolution imaging of neural currents from MEG data using an explicit piecewise image model," 3rd IEEE International Symposium on Biomedical Imaging: Nano to Macro, 2006.*
Holmes, "Bayesian radial basis functions of unknown dimension," Imperial College Report, 28 pages, 1997.*
Tilg, "Model-based imaging of cardiac electrical excitation in humans," Medical Imaging, IEEE Transactions, vol. 21(9), p. 1031-1039, 2002.*
Henshall, "Optimizing electrode and filter selection in cochlear implant speech processor maps," Journal-American Academy of Audiology, vol. 12.9, p. 478-489, 2001.*
Ahmad GF et al.; "Joint energy and laplacian regularization in the the inverse problem of electrocardiography"; Mar. 1994 (Mar. 1994) pp. 59-62; retrieved from the internet URL:http://ieeexplore.ieee.org/xplarticle; retrieved on May 13, 2014.
Invitation to pay additional fees with annex to form PCT/ISA/206 in PCT Application No. PCT/US2014/021858 (Jun. 6, 2014).
International Search Report and Written Opinion in PCT Application No. PCT/US2014/021858 (dated Sep. 9, 2014).

* cited by examiner

*Primary Examiner* — G. Steven Vanni
(74) *Attorney, Agent, or Firm* — Dykema Gossett PLLC (57) ABSTRACT

An embodiment of a method for solving the inverse problem of electrophysiology and determining a voltage distribution on a surface of a tissue may comprise receiving a plurality of voltages collected by a plurality of electrodes adjacent to the surface, discretizing the problem using a Finite Element Method (FEM) or a Boundary Element Method (BEM), introducing one or more regularization terms to an error minimization formulation, and solving, by a processor, the voltage distribution according to the plurality of voltages and according to the regularization terms. The regularization terms may comprise one or more of a Laplacian smoothness operator, a Tikhonov regularization matrix, a confidence matrix, and a linear operator that interpolates the plurality of electrode voltages to the tissue voltage distribution.

13 Claims, 7 Drawing Sheets

LAPLACIAN AND TIKHONOV REGULARIZATION FOR VOLTAGE MAPPING WITH A MEDICAL DEVICE

BACKGROUND a. Technical Field

The instant disclosure relates generally to mapping of electrical activity within a human body, including the mapping of electrical activity in cardiac tissue.

b. Background Art

Mapping the electrical activity of the heart (i.e., determining the voltage distribution over the heart tissue surface) can be used to examine and diagnose heart activity, such as to detect abnormalities, including arrhythmia. Such electrical activity can be projected onto a map or model of the heart to create, for example, an activation map.

One known way of mapping the electrical activity of the heart is through contact-based mapping, in which one or more electrodes are placed in contact with heart tissue to capture the electrical activity of a particular tissue location. Contact-based procedures, though, can be very time-consuming, as electrical activity at many locations may need to be measured, and the electrode needs to be placed in contact with the tissue at each of those locations. Accordingly, non-contact mapping procedures have been developed.

A non-contact mapping procedure may involve placing a catheter with a large number of electrodes within the heart. One known device for non-contact mapping procedures is the Ensite™ Array™ catheter commercially available from St. Jude Medical, Inc. of St. Paul, Minn. The non-contact mapping catheter may include a basket structure, on which the electrodes are disposed, that may be collapsed for navigation to the interior of the heart and expanded within the heart to perform a mapping procedure. Using a non-contact mapping catheter, electrical activity of the heart may be assessed much more quickly than in a contact-based procedure.

An important element of non-contact mapping is relating voltages on the catheter electrodes to the electrical activity of adjacent heart tissue. This problem, solving for a distribution of voltage over the surface of the heart given a finite set of observed voltages on or in a conducting medium surrounding or within the heart, is colloquially referred to as the inverse problem of electrocardiography. The inverse problem is ill-posed because: (1) the number of observed voltages (i.e., the number of electrodes used to collect measurements) is often less than the number of cardiac surface locations where voltage is to be solved (allowing for non-unique solutions to the problem); and (2) the observed voltages reflect a spatially-averaged version of cardiac surface voltage (making the problem ill-conditioned).

BRIEF SUMMARY

An embodiment of a method for solving the inverse problem of electrophysiology and determining a voltage distribution on a surface of a tissue may comprise receiving a plurality of voltages collected by a plurality of electrodes adjacent to the surface, discretizing the problem using a Finite Element Method (FEM) or a Boundary Element Method (BEM), introducing one or more regularization terms, and solving, by a processor, the voltage distribution according to the plurality of voltages and according to the regularization terms. A first of the regularization terms may comprise a Laplacian smoothness operator and another of the regularization terms may comprise a Tikhonov regularization matrix.

Another embodiment of a method for determining a voltage distribution on a surface of a tissue may comprise receiving a plurality of voltages collected by a plurality of electrodes adjacent to the surface, discretizing the problem using a Finite Element Method (FEM) or a Boundary Element Method (BEM), introducing one or more regularization terms, and solving, by a processor, the voltage distribution according to the plurality of voltages and according to the regularization terms. One of the inverse solution and the regularization terms may comprise a confidence matrix, wherein one or more terms of the confidence matrix are associated with one or more of a known probability that one or more of the plurality of voltages accurately measures a portion of the voltage distribution and a known or assumed confidence value for one or more portions of the reconstructed voltage distribution.

Another embodiment of a method for determining a voltage distribution on a surface of a tissue may comprise receiving a plurality of voltages collected by a plurality of electrodes adjacent to the surface, discretizing the problem using a Finite Element Method (FEM) or a Boundary Element Method (BEM), introducing one or more regularization terms, and solving, by a processor, the voltage distribution according to the plurality of voltages and according to the regularization terms. One of the regularization terms may comprise a linear operator that interpolates the plurality of electrode voltages to the tissue voltage distribution, wherein the linear operator is other than an identity matrix.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
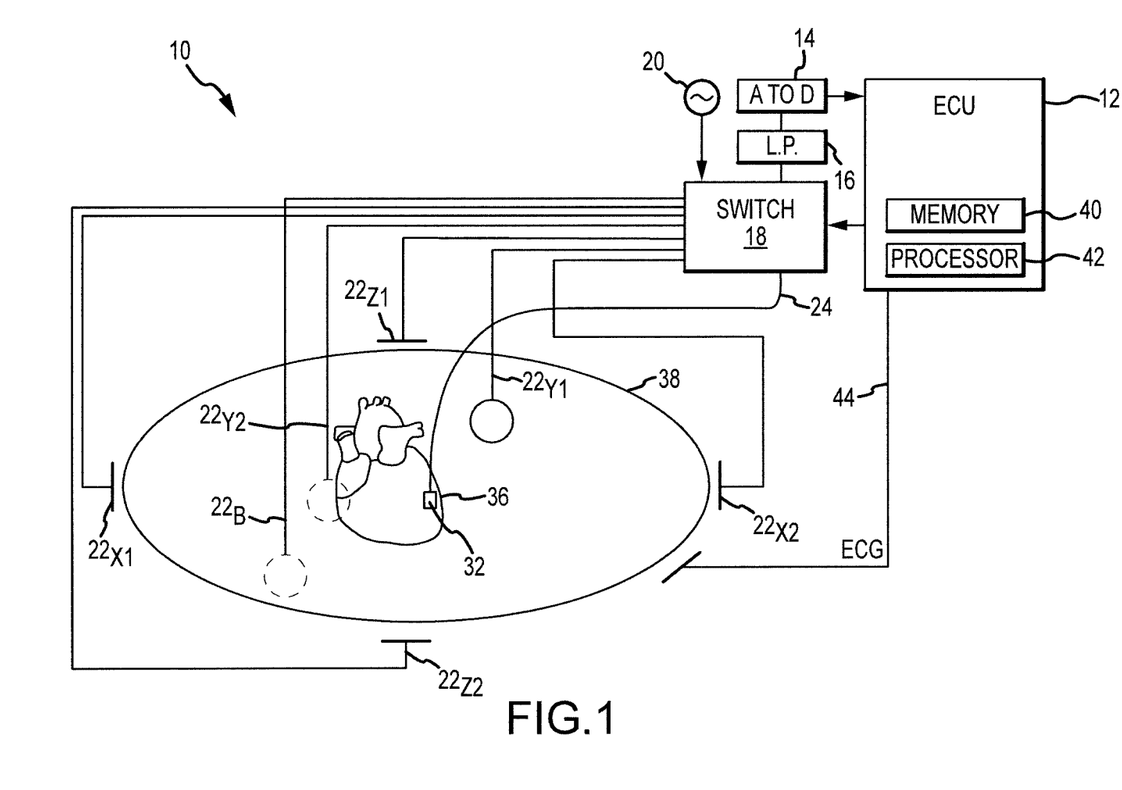
FIG. 1 is a diagrammatic depiction of an exemplary mapping and navigation system.
Figure 2A:
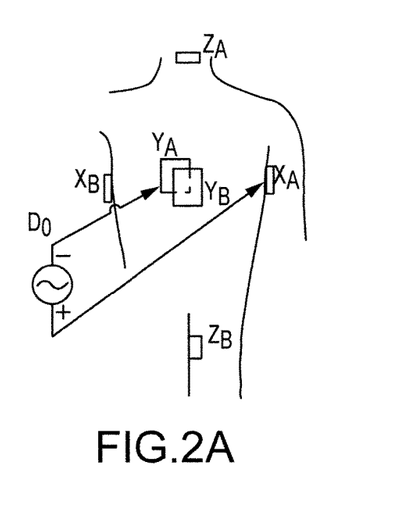
FIGS. 2A-2D are schematic diagrams of exemplary dipole pairs of driven body patch electrodes suitable for use with the mapping and navigation system of FIG. 1.
Figure 2B:
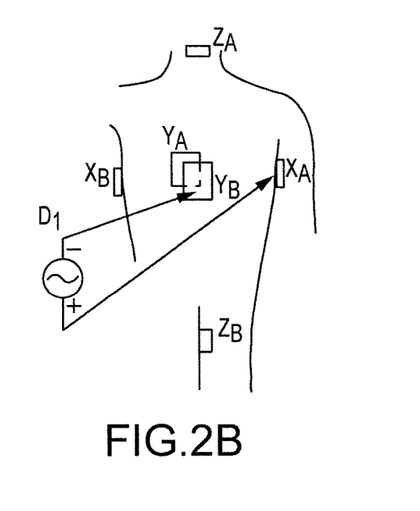
Figure 2C:
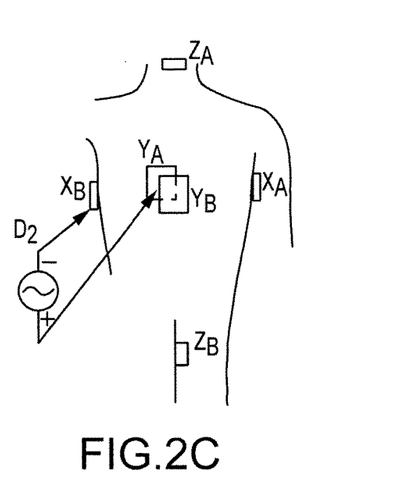
Figure 2D:
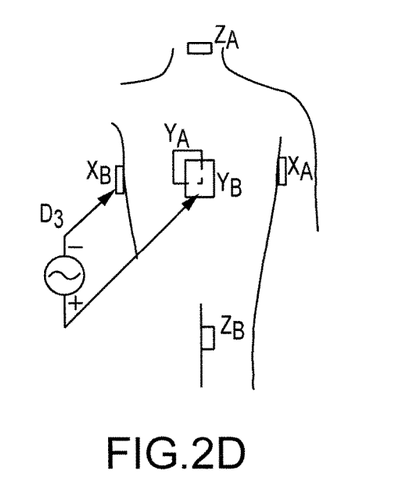

Referring now to the figures, in which like numerals indicate the same or similar elements in the various views, FIG. 1 is a diagrammatic depiction of an embodiment of an exemplary mapping and navigation system 10. The system may include various visualization, mapping and navigation components as known in the art, including, for example, an EnSite™ Velocity™ system commercially available from St. Jude Medical, Inc., or as seen generally, for example, by reference to U.S. Pat. No. 7,263,397, or U.S. Patent Publication No. 2007/0060833, both of which are hereby incorporated by reference in their entireties as though fully set forth herein.

The system 10 may include an electronic control unit (ECU) 12, an analog-to-digital converter (A-to-D) 14, a lowpass filter (.L.P.) 16, a switch 18, a signal generator 20, and a plurality of body surface patch electrodes 22. The system 10 may be electronically and/or mechanically coupled with an elongate medical device 24. The medical device 24 may be, in an embodiment, a non-contact mapping catheter (i.e., mapping catheter 24). The system 10 will be described with reference to an embodiment in which the elongate medical device 24 is a noncontact mapping catheter 24 configured to sense voltages from endocardial tissue within the heart. It should be understood, however, that the system 10 is not so limited, and may additionally or alternatively be used for sensing voltages from epicardial tissue or other anatomical structures within the body.

Figure 3:
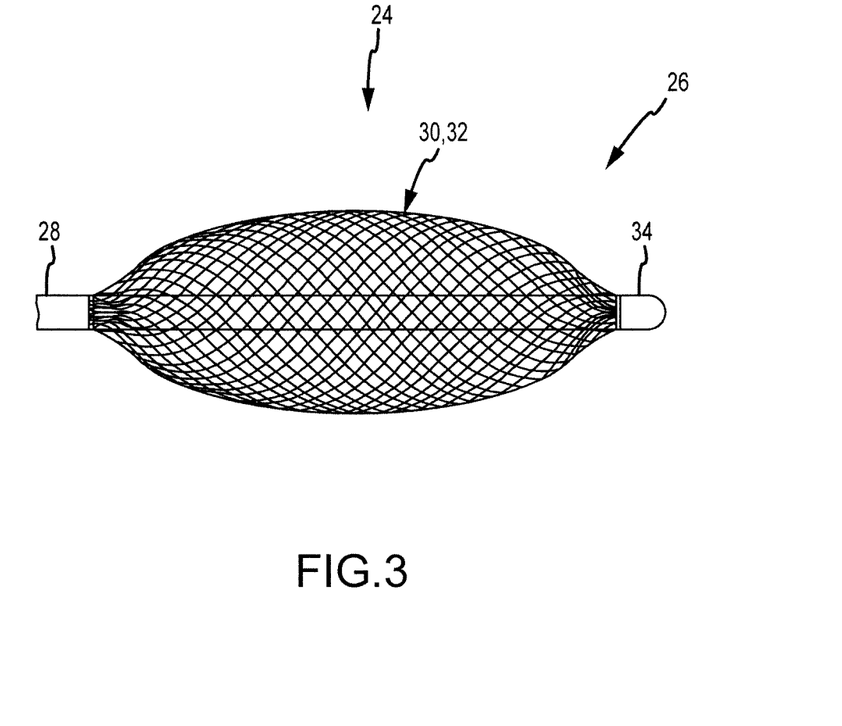
FIG. 3 is a plan view of a distal end portion of an exemplary noncontact mapping catheter.

FIG. 3 is a plan view of a distal end portion 26 of an exemplary noncontact mapping catheter 24. In the embodiment of FIG. 3, the catheter 24 comprises a shaft 28 that extends from a proximal end portion (not shown) to the distal end portion 26. The distal end portion 26 may include or may be coupled to a basket assembly 30, the basket assembly 30 comprising a plurality of electrodes 32, and a tip electrode 34. The electrodes 32, 34 may be used, for example and without limitation, for determining the position of the distal end portion 26 and the specific electrodes 32, 34 as described below, for mapping the electrical activity of anatomical structures (such as the heart), and for delivering energy, such as ablation energy. The basket assembly 30 may comprise a plurality of splines that, in an embodiment, are configured to collapse for the distal end portion 26 to be guided through an introducer (not shown) and, upon extension out of the introducer, to expand to the configuration shown in FIG. 3. By way of example only, the basket assembly 30 may, in embodiments, include any number of electrodes 32, such as thirty-two (32) electrodes or sixty-four (64) electrodes. Furthermore, the electrodes 32 may be complemented by additional electrodes on one or more other medical devices within the heart (not shown) for sensing myocardial voltages. Together, these electrodes may provide information for BEM or FEM modeling, an inverse solution, and regularization.

Referring again to FIG. 1, the system 10 may be configured to provide, among other things, mapping of patient tissue, such as one or more chambers of the heart 36 of a patient 38. Accordingly, the ECU 12 may be configured to receive electrical measurements from one or more electrodes 32 (diagrammatically shown as a single electrode 32 in FIG. 1) on the mapping catheter 24 and, based on those measurements, to assess one or more electrical characteristics of tissue surrounding the distal end of the mapping catheter 24. In an embodiment, the ECU 12 may be configured to determine a voltage distribution of an endocardial surface according to electrical measurements from the mapping catheter electrodes 32, as described below in conjunction with FIGS. 4-7. The ECU 12 may be further configured to determine that voltage distribution with respect to an anatomical model, such as a model of one or more chambers, features, and/or surfaces of a heart 36. In an embodiment, the model may be a model constructed according to the Boundary Element Method (BEM). The Boundary Element Method uses area elements to construct a matrix expression relating voltages measured on the mapping catheter electrodes 32 to voltages in the endocardial, myocardial, or epicardial tissue. This matrix expression depends on the cardiac surface and sensing electrode positions with respect to that surface and describes the "forward" map from cardiac surface voltages to sensing electrode voltages. The solution to the "inverse" problem (from sensed electrode voltages to cardiac surface voltages) is a matrix equation incorporating the BEM forward map and regularization terms as described further below. Accordingly, the ECU 12 may be configured to determine a voltage distribution by determining a voltage for one or more surfaces, vertices, nodes, or other features of a BEM model.

The ECU 12 may include a non-volatile memory 40 and a processor 42 configured to perform many of the functions and operations described herein—i.e., the memory 40 may store instructions for performing portions of one or more methods described herein (i.e., the methods illustrated in FIGS. 4-7), and the processor 42 may be configured to execute those instructions to perform the methods. The memory 40 may also be configured to store an anatomical model, such as a BEM model, a plurality of measurements from the mapping catheter 24, a plurality of terms and values for the methods described below, and other data and information. In an embodiment, the ECU 12 may additionally or alternatively comprise a field-programmable gate array (FPGA) and/or other known computing device.

In addition to (and as a part of) electrophysiology mapping, the system 10 may be configured to determine the position and orientation (P&O) of the medical device 24 (e.g., of the distal end portion 26) within the body. Accordingly, the ECU 12 may be configured to control generation of one or more electrical fields and determine the position of one or more electrodes (e.g., electrodes 32) within those fields. The ECU 12 may thus be configured to control signal generator 20 in accordance with predetermined strategies to selectively energize various pairs (dipoles) of body surface patch electrodes 22, as described in greater detail below. In operation, the ECU 12 may (1) obtain raw patch data (i.e., voltage readings) via the filter 16 and A-to-D converter 14 and (2) use the raw patch data (in conjunction with electrode measurements) to determine the raw, uncompensated, electrode location coordinates of the electrodes 32 positioned inside the heart 36 or a chamber thereof in three-dimensional space. The ECU 12 may be further configured to perform one or more compensation and adjustment functions, and to output a location of the electrodes 32. Motion compensation may include, for example, compensation for respiration-induced patient body movement, as described in U.S. patent application publication no. 2012/0172702, which is hereby incorporated by reference in its entirety.

The body surface patch electrodes 22 may be used to generate axes-specific electric fields within the body 38, and more specifically within the heart 36. Three sets of patch electrodes may be provided: (1) electrodes $22_{X1}$, $22_{X2}$, (X-axis); (2) electrodes $22_{Y1}$, $22_{Y2}$, (Y-axis); and (3) electrodes $22_{Z1}$, $22_{Z2}$, (Z-axis). Additionally, a body surface electrode ("belly patch") $22_B$, may be provided as an electrical reference. Other surface electrode configurations and combinations are suitable for use with the present disclosure, including fewer electrodes 22, more electrodes 22, or different physical arrangements, e.g. a linear arrangement instead of an orthogonal arrangement.

Each patch electrode 22 may be independently coupled to the switch 18, and pairs of patch electrodes 22 may be selected by software running on the ECU 12 to couple the patch electrodes 22 to the signal generator 20. A pair of electrodes, for example the Z-axis electrodes $22_{Z1}$, $22_{Z2}$, may be excited by the signal generator 20 to generate an electrical field in the body 38 of the patient and, more particularly, within the heart 36. In one embodiment, this electrode excitation process occurs rapidly and sequentially as different sets of patch electrodes 22 are selected and one or more of the unexcited surface electrodes 22 are used to measure voltages. During the delivery of the excitation signal (e.g., current pulse), the remaining (unexcited) patch electrodes 22 may be referenced to the belly patch $22_B$ and the voltages impressed on these remaining electrodes 22 may be measured. In this fashion, the patch electrodes 22 may be divided into driven and non-driven electrode sets. The low pass filter 16 may process the voltage measurements. The filtered voltage measurements may be transformed to digital data by the analog to digital converter 14 and transmitted to the ECU 12 for storage (e.g. in the memory 40) under the direction of software. This collection of voltage measurements may be referred to herein as the "patch data." The software may have access to each individual voltage measurement made at each surface electrode 22 during each excitation of each pair of surface electrodes 22.

The patch data may be used, along with measurements made at the electrodes 32, to determine a relative location of the electrodes 32. The patch data may also be used along with measurements made at the tip electrode 34 and/or other electrodes on the catheter 24 or on another device to determine a relative location of the tip electrode 34 and/or the other electrodes. The discussion above and below describes determining the location of the electrodes 32, but it should be understood to apply to the tip electrode 34 and other electrodes, as well. In some embodiments, potentials across each of the six orthogonal patch electrodes 22 may be acquired for all samples except when a particular surface electrode pair is driven. In embodiments, sampling a voltage with a particular patch electrode 22 while a surface electrode 22 acts as a source or sink in a driven pair may be avoided, as the potential measured at a driven electrode during this time may be skewed by the electrode impedance and the effects of high local current density. In an alternate embodiment, however, sampling may occur at all patch electrodes 22, even those being driven.

Generally, in an embodiment, three nominally orthogonal electric fields may be generated by a series of driven and sensed electric dipoles in order to determine the location of the catheter 24 (i.e., of the electrodes 32). Alternately, these orthogonal fields can be decomposed and any pair of surface electrodes (e.g., non-orthogonal) may be driven as dipoles to provide effective electrode triangulation.

FIGS. 2A-2D show a plurality of exemplary non-orthogonal dipoles, designated $D_0$, $D_1$, $D_2$ and $D_3$. In FIGS. 2A-2D, the X-axis surface electrodes are designated $X_A$ and $X_B$, the Y-axis surface electrodes are designated $Y_A$ and $Y_B$, and the Z-axis electrodes are designated $Z_A$ and $Z_B$. For any desired axis, the potentials measured across an intra-cardiac electrode 32 resulting from a predetermined set of drive (source-sink) configurations may be combined algebraically to yield the same effective potential as would be obtained by simply driving a uniform current along the orthogonal axes. Any two of the patch electrodes 22 may be selected as a dipole source and drain, as noted above, with respect to a ground reference, e.g., belly patch $22_B$, while the unexcited body patch electrodes 22 measure voltage with respect to the ground reference. The electrodes 32 placed in heart 36 are also exposed to the field from a current pulse and voltages on the electrodes 32 are individually and separately measured with respect to ground, e.g., belly patch $22_B$.

Referring again to FIG. 1, data sets from each of the patch electrodes 22 and the electrodes 32 are all used to determine the location of the electrodes 32 within the heart 36. After the voltage measurements are made for a particular set of driven patch electrodes 22, a different pair of patch electrodes 22 may be excited by the signal generator 20 and the voltage measurement process of the remaining patch electrodes 22 and electrodes 32 takes place. The sequence may occur rapidly, e.g., on the order of 100 times per second in an embodiment. To a first approximation the voltage on the electrodes 32 within the heart bears a linear relationship with position between the patch electrodes 22 that establish the field within the heart 36, as more fully described in U.S. Pat. No. 7,263,397 referred to above.

Some or all of the conventional twelve (12) ECG leads, coupled to additional body patches and designated collectively by reference numeral 44, may be provided to support the acquisition of an electrocardiogram (ECG) of the patient. As shown, ECG leads 44 may be coupled directly to the ECU 12 for acquisition and subsequent processing to obtain the phase of the heart in the cardiac cycle. Cardiac phase information may be used, in an embodiment, in mapping of electrical activity of the heart 36, as described below.

In summary, FIG. 1 shows an exemplary system 10 that employs seven body patch electrodes 22, which may be used for injecting current and sensing resultant voltages. Current may be driven between two patches 22 at any time. Measurements may be performed between a non-driven patch 22 and, for example, belly patch $22_B$ as a ground reference. A patch bio-impedance, also referred to as a "patch impedance", may be computed according to the following equation:

$$BioZ[n \to m][k] = \frac{V_k}{I_{n \to m}}$$

where $V_k$ is the voltage measured on patch k and $I_{n \to m}$ is a known constant current driven between patches n and m. The position of an electrode 32 may be determined by driving current between different sets of patches and measuring one or more patch impedances. In one embodiment, time division multiplexing may be used to drive and measure all quantities of interest. Position determining procedures are described in more detail in, for example, U.S. Pat. No. 7,263,397 and publication no. 2007/0060833 referred to above.

To perform an electrophysiology (e.g., mapping) procedure, the distal end portion 26 of the catheter 24 may be manually guided to a desired location by a physician. Additionally or alternatively, the catheter 24 may be coupled with and directed by a remote catheter guidance system (RCGS), such as a robotic RCGS. For example, the catheter 24 may be incorporated into a robotic system as described in U.S. Pat. Nos. 8,317,744 and 8,317,745 and U.S. patent application publication nos. 2009/0247943; 2009/0247993; and 2010/0073150, all of which are hereby incorporated by reference in their entireties as though fully set forth herein.

In addition to determining the positions of the electrodes 32, the system 10 may also be provided for assessing the electrical activity of the heart, for example. Accordingly, the ECU 12 may be further configured to perform one or more steps in one or more methods of determining a voltage distribution on a cardiac surface. The following discussion of such methods will be with respect to determining a voltage distribution on an endocardial surface according to non-contact measurements taken from within the heart 36, but it should be understood that neither the methods below nor the system 10 above are so limited. One or more of the steps of the methods described below may be performed by the ECU 12 (e.g., embodied in software stored in the memory 40 and executed by the processor 42), in an embodiment.

Figure 4:
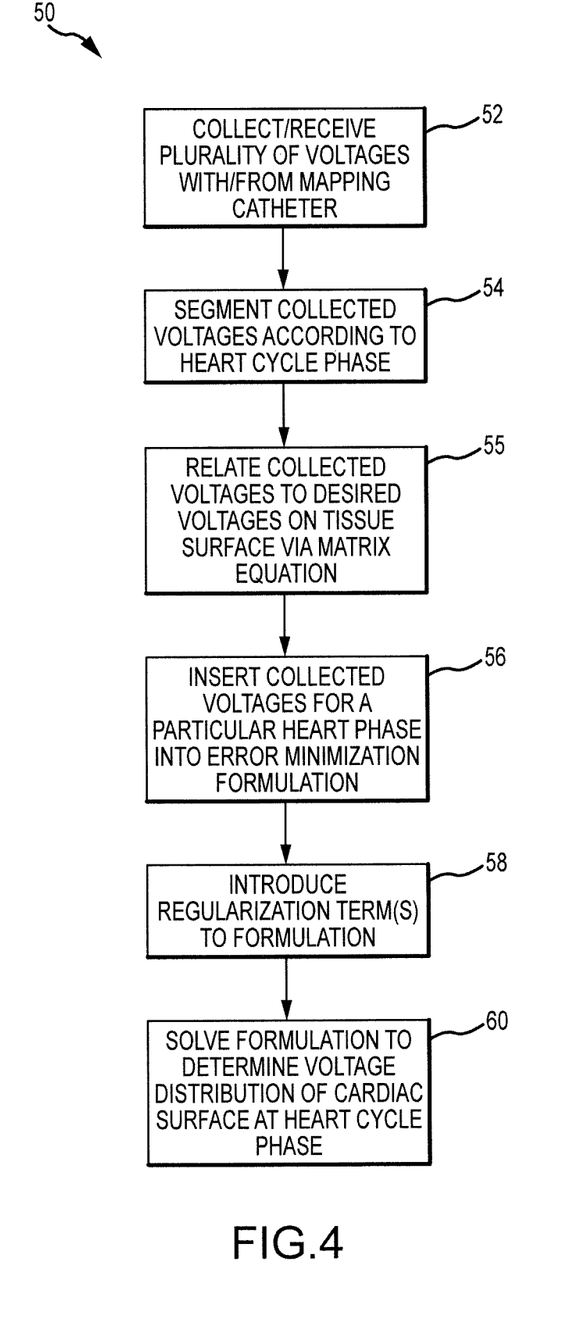
FIG. 4 is a flow chart depicting an exemplary method of determining a voltage distribution on the surface of the heart.

FIG. 4 is a flow chart illustrating a generalized method 50 for determining a voltage distribution on an endocardial surface in accordance with an exemplary embodiment. In the field of catheter mapping and ablation of arrhythmias, the most common cardiac surface of interest is the endocardium, in which the conducting medium is blood. However, approaches similar to the methods described below may be used for epicardial voltage mapping from body surface potentials, or for voltage mapping of anatomical structures within the body. The methods described herein may also be used for deriving other physiological parameters of interest within the body in addition to, or in lieu of, voltage, such as activation timing or low voltage regions representing scar tissue, valve orifices, or blood vessel ostia, for example.

The method 50 may begin with a voltage collection step 52 involving collecting a plurality of voltages with, or receiving a plurality of voltages from, a mapping catheter (e.g., the non-contact mapping catheter 24 illustrated in FIG. 3) adjacent to the surface of the heart (e.g., within a chamber of the heart, adjacent to the endocardium). Each of the plurality of voltages may be respective of (i.e., measured by) an electrode 32 on the mapping catheter 24. The voltages may be voltages present in the blood within a heart chamber, indicative of electrical activity of adjacent tissue (e.g., the endocardial surface within the chamber). In an exemplary embodiment of the voltage collection step 52, the ECU 12 (see FIG. 1) may detect and record a number of sets of voltages with the mapping catheter 24 throughout a heart cycle. The voltages may be stored by the ECU 12 (e.g., in the memory 40) for further processing.

The voltages collected in the voltage collection step may be collected in conjunction with (i.e., synchronized with) an organ timing signal (such as an ECG) and the positions of the electrodes used to collect the voltages. Accordingly, each collected voltage may be associated with a position and a particular organ timing state (e.g., a portion of a cardiac cycle).

As part of or before the voltage collection step 52, a physician may manually guide a medical device (e.g., the mapping catheter 24) to a desired location within the patient's body (e.g., a particular chamber of the heart). Alternatively or additionally, an RCGS may be used to direct movement of one or more medical devices, as described above.

In a segmentation step 54, the collected voltages may be segmented or gated according to an interval of time in which they were collected (e.g., a first interval of voltages associated with atrial but not ventricular depolarization, or a second interval of voltages collected during ventricular depolarization belonging to a specific ventricular arrhythmia, etc.). Heart cycle intervals or phases may be determined according to electrocardiogram data, in an embodiment.

In a discretization step 55, the collected voltages from the mapping catheter 24 are related to the desired voltages on the cardiac surface via a matrix expression A constructed using a Finite Element Method (FEM) or a Boundary Element Method (BEM). In an embodiment, a separate matrix expression may be constructed for each particular heart cycle interval or phase.

In a formulation step 56, the plurality of matrix equations may be analyzed using an error minimization formulation, such as a least squares formulation. The following discussion will be with respect to embodiments in which least squares formulations are employed, but it should be understood that other known error minimization techniques such as $L_1$ formulations may be used without departing from the spirit and scope of this disclosure. The least squares formulation may be solved, for example, to determine the voltage distribution on the endocardial surface. The least squares formulation may be solved separately for each heart cycle phase for which data was collected in the voltage collection step 52, in an embodiment.

As noted above, the problem of solving the endocardial voltage distribution (which may have thousands of points or portions for which a voltage is desired) according to voltages collected with a non-contact mapping catheter (which may have a relatively small number of electrodes such as, for example, sixty-four (64) electrodes) is ill-posed. Accordingly, at an introduction step 58, a number of regularization terms may be introduced into the least-squares inverse solution formulation. It should be understood that, although the formulation step 56 and the introduction step 58 are discussed herein as separate steps, such separation is for ease of description and to highlight that the use of the schemes, approaches, algorithms, and terms discussed herein. In practice, however, the error minimization formulation selected to solve the voltage distribution may have regularization terms included, without separate processes of selecting the formulation and the regularization terms.

Including the selected error minimization formulation and the introduced regularization terms, the resulting least-squares formulation for regularization of the ill-posed "inverse problem of electrocardiography" can be written as a cost function involving two terms: 1) a penalty of solutions $v_e$ that are not consistent with observed probe voltages $v_p$, and 2) one or more regularization terms that incorporate constraints and/or knowledge of solutions $v_e$. An exemplary formulation is shown as Equation (1) below:

$$v_e^* = \arg\min_{v_e}\{\|Av_e - v_p\|_P^2 + \Sigma_{i=1}^N \lambda_i^2 \|L_i v_e - b_i\|_{Q_i}^2\} \quad (1)$$

In Equation (1) and subsequent equations herein, $v_p$ is a vector containing collected electrode voltages, with length determined by the number of electrodes 32 on the mapping catheter 24 and/or other devices used to collect voltages. In some embodiments, for example, $v_p$ may be a 64-element vector if collected with a device with sixty-four (64) electrodes. The term $v_e^*$ in Equation (1) is a vector of the optimal endocardial voltage distribution with a number of terms determined by the number of locations on the endocardial surface for which a voltage is to be solved, which may be in the thousands (e.g., $v_e^*$ may have length 2000 or more, in embodiments), and which may be related to a number of nodes or other features of a model of the endocardium, such as a BEM model, in an embodiment. The term $v_e$ is a particular vector of the endocardial voltage distribution that has the same length as $v_e^*$. A is a BEM forward transfer matrix that maps the endocardial voltage distribution onto the measured voltages at electrodes 32, such that $Av_e = v_p$. P is an inverse covariance (or confidence) matrix of the error in $v_p$. Each $L_i$ is a regularization matrix operating on $v_e$. Each $Q_i$ is an inverse covariance (or confidence) matrix of the error in $v_e$. Each $b_i$ is a vector of the expected value of a regularization term; for example, $b_i$ could be a set of known endocardial voltages. Each $\lambda_i$ is a weighting parameter that may allow the solution to be adjusted between a solution that is more accurate on a voltage-by-voltage basis, or a solution that is smoother, for example. N is the number of regularization terms used, which may vary among embodiments.

P, $Q_i$, N, $L_i$, $\lambda_i$, and $b_i$ may be or may include predetermined values—i.e., values determined before the voltage collection step or otherwise independent of the values in $v_v$, in an embodiment. These values may be selected or predetermined for a particular regularization scheme. For example, a number of different approaches or methods associated with the introduction step, each of which will be discussed in further detail below, and which may be combined with each other, and in some embodiments, may be associated with particular values. First and second approaches may involve selection of values for the matrix P. A third approach, referred to herein as "La-Ti," is discussed in conjunction with FIG. 5. A fourth approach, referred to below as "Confidence Power," is discussed in conjunction with FIG. 6. A fifth approach, referred to below as "vProbe," is discussed in conjunction with FIG. 7. Each of these approaches may be used to select values for one or more of P, $Q_i$, N, $L_i$, $\lambda_i$, and $b_i$. Furthermore, as will be apparent from the discussion below, elements of the different approaches may be combined, in embodiments.

Selecting Values for Matrix P.

As part of the introduction step 56, values for P may be selected. The positive semidefinite matrix P defines a vector norm for the discrepancy or error $e_p$ between observed probe voltages $v_p$ and predicted voltages based on the endocardial voltages $v_e$ and the forward BEM solution matrix A. Since $e_p = Av_e - v_p$, it follows that $\|Av_e - v_p\|_P^2 = \|e_p\|_P^2 = e_p^T P e_p$. Throughout this disclosure, a superscript T indicates the transpose of the underlying vector or matrix.

In some embodiments, according to a first approach, matrix P may be selected to be equal to the identity matrix I (i.e., P=I). In other embodiments, according to a second approach, a more complex matrix P may be selected to achieve a more balanced and optimal solution. If one or more electrodes 32 used to collect the measured voltages in matrix $v_p$ are "bad" (e.g., electrically disconnected, experiencing frequent and/or severe measurement artifacts from electrode-electrode contact, or otherwise malfunctioning), the elements (i.e., rows and columns) of P corresponding to these electrodes may be set to zero upon a determination that the electrodes 32 are inoperable. Electrodes 32 may be identified as inoperable automatically (e.g., by a routine executed by the ECU 12) and/or manually (e.g., by a physician observing the data reported by the electrodes 32).

Most generally, P is an inverse covariance matrix which captures a priori knowledge of uncertainty or noise of probe electrodes 32 and the covariance/correlation of noise resulting from electrodes 32 which are near each other. The introduction of P, known as a "whitening filter" in some disciplines, sets up the least squares formulation embodied in Equation (1) as the maximum likelihood solution under broadly applicable assumptions of multivariate normal distributions of error.

Once values are chosen for P, $Q_i$, N, $L_i$, $\lambda_i$, and $b_i$, the method 50 may further include a solution step 60 that includes determining the voltage distribution on the endocardial surface according to the collected voltages and the introduced regularization terms by solving the error minimization formulation. As part of the solution step 60, Equation (1) may be differentiated over $v_e$, set equal to zero, and solved. Software capable of and configured to find a solution is known in the art. In some embodiments, the software comprises a set of software instructions or code stored memory 40 and executed by the processor 42 of ECU 12.

As noted above, the formulation step 56, introduction step 58, and solution step 60 may be performed for a number of cardiac models associated with a number of different intervals or phases of a cardiac cycle. The electrical behavior of the heart, or of one or more chambers or portions of the heart, may thus be determined for all relevant portions of a heart cycle, in an embodiment. Once determined, the voltage distribution for one or more portions of a heart cycle may be used to create an activation map and/or other known representations of cardiac activity. Such representations may be displayed on or with a model of the heart.

Although there are many possible ways to incorporate constraints and prior knowledge into regularized solutions for the inverse problem of electrophysiology, the methods described herein (i.e., as generally represented by Equation (1) and as shown with further specificity below) are particularly effective. An error minimization formulation such as a least squares formulation is both readily computable and rigorously supportable with assumptions on the distribution of uncertainty and noise. The regularization schemes described herein are, in many respects, more robust than Tikhonov regularization, which is widely used for solving BEM problems in non-contact mapping. Tikhonov regularization is formulated as shown in Equation (2) below:

$$v_e^* = \arg\min_{v_e}\{\|Av_e - v_p\|^2 + \lambda^2\|v_e\|^2\} \quad (2)$$

By introducing one or more of the additional regularization terms P, $Q_i$, N, $L_i$, and $b_i$, the methods described herein give a more accurate and robust solution than known regularization schemes.

Selecting Values for $Q_i$, N, $L_i$, $\lambda_i$, and $b_i$—"La-Ti Regularization."

Figure 5:
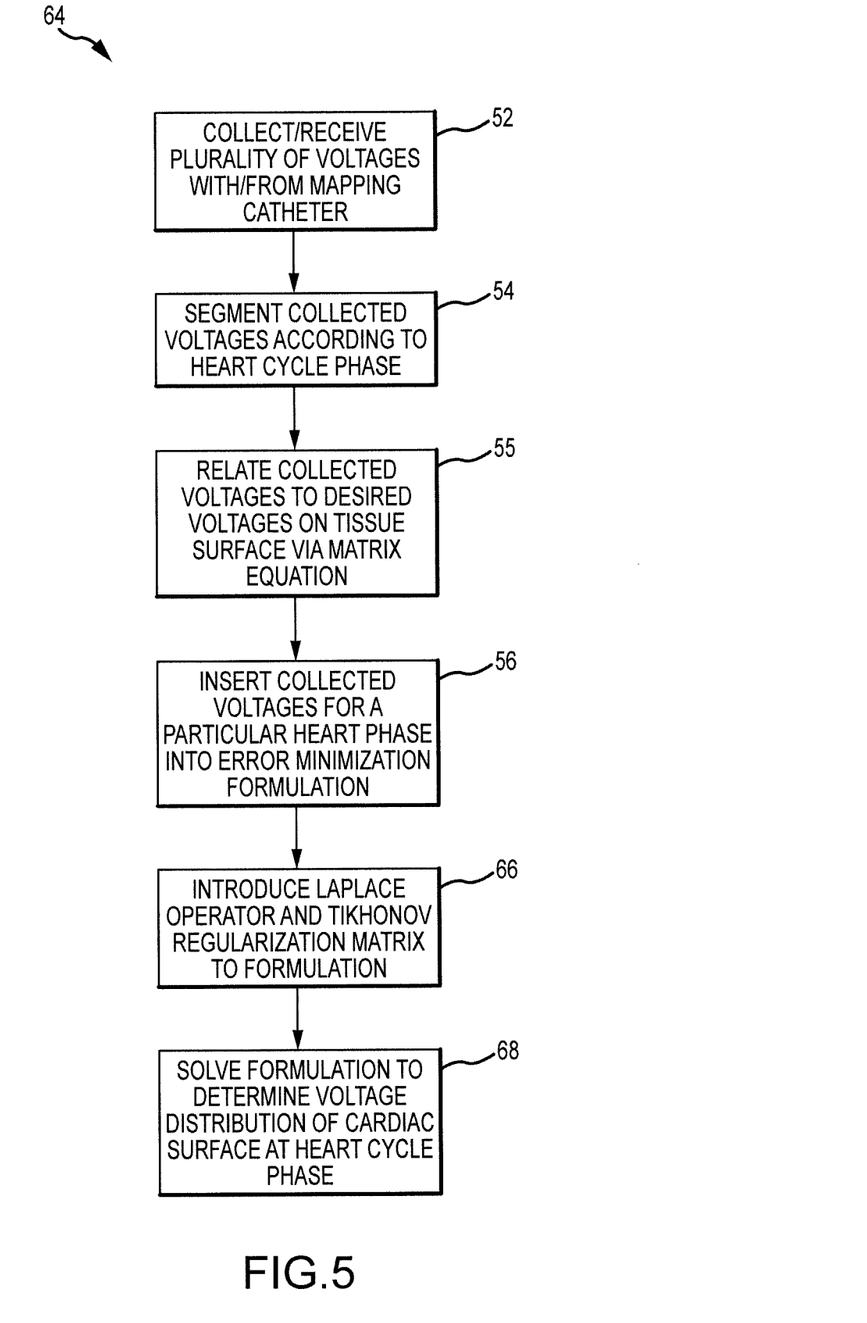
FIG. 5 is a flow chart depicting an exemplary method of determining a voltage distribution on the surface of the heart.

FIG. 5 is a flow chart illustrating an exemplary method 64 of determining a voltage distribution on the surface of the heart. The method 64 illustrated in FIG. 5 is a specific embodiment of the method 50 illustrated in FIG. 4. The method 64 illustrated in FIG. 5 employs the Laplacian-Tikhonov, or "La-Ti" regularization scheme. The La-Ti regularization scheme, as its name implies, is a blend of Laplacian regularization, which is effective for smoothing, and Tikhonov regularization, which is effective for penalizing extreme endocardial voltages (i.e., extreme outliers). Laplacian regularization often does better than Tikhonov regularization at reconstructing hotspot amplitudes and locations and at reducing spatial "noise" in maps. However, Laplacian regularization can sometimes result in large, nonphysical oscillations in the voltage solution on the portion of the cardiac surface that is furthest from the measurement electrodes. Tikhonov regularization, on the other hand, penalizes nonphysical values (i.e., extreme outliers), but with little regard to smoothness, and may thus result in an unnaturally noisy or "blotchy" solution. A blended Laplacian and Tikhonov regularization scheme may include the advantages of both approaches and result in a smooth solution that adequately discards outlying measurements.

The method 64 may begin, like the broader method 50, with a voltage collection step 52, a segmentation step 54, a discretization step 55, and a formulation step 56, which may be performed as described above with respect to the broader method 50. The method 64 may continue to an introduction step 66 that includes introducing to the error minimization formulation a Laplacian operator and a Tikhonov regularization matrix, as explained below.

As a specific embodiment of the formulation shown above in Equation (1), La-Ti regularization may use N=2, where $L_1$=I (where I again is the identity matrix, as in Tikhonov regularization) and $L_2$ is the discrete Laplacian smoothness operator L on the endocardial surface. In embodiments, $b_2$=0, since the curvature of wavefronts and instantaneous voltages are not known. In other embodiments, $b_1$ may include a set of known endocardial voltages or other a priori knowledge respective of the endocardium. For example, $b_1$ may include, for La-Ti regularization and other schemes described herein, one or more voltages determined based on a previously-solved voltage distribution for another portion of the heart cycle.

Laplacian smoothing naturally introduces, into the endocardial voltage distribution, the tendency for wavefronts to exist and spread in a smooth, contiguous fashion. This occurs through the regularization term $\|Lv_e\|_{Q_2}^2$, where $Q_2$ may be a diagonal matrix with, for example, low values at anatomic regions known for focal activity (e.g., the sinoatrial node). If, on the other hand, focal sites of arrhythmia activation are not known ahead of time, $Q_2$ may be the identity matrix.

As noted above, Tikhonov regularization penalizes outlier values. This occurs through the regularization term $\|v_e\|_{Q_1}^2$ (as noted above, in La-$T_1$, $L_1$=I may be used), where $Q_1$ may be the identity matrix or may be a diagonal matrix with, for example, high values for locations on the surface of the BEM solution where no activation occurs (such as, for example only, valve orifices and vein ostia) and low values where the depolarization signal amplitude is expected to be high (such as, for example only, the ventricles). Non-uniform Tikhonov regularization may also be employed to compensate for BEM mesh nonuniformity—recognizing that Tikhonov regularization could inappropriately penalize locations where the BEM mesh grid spacing is small, $Q_1$ may assign less weight to area elements or facet lengths associated with relatively small grid spacing. In other words, $Q_1$ may more strongly regularize portions of the voltage distribution associated with a larger grid spacing on a BEM model, and less strongly regularize portions associated with smaller grid spacing.

As noted above, a goal of La-Ti regularization is to combine the best features of Laplacian and Tikhonov regularization. This is made rigorous by noting that amplitude and smoothness constraints are largely independent and, by the rules of probability, this implies multiplication of the associated probability distribution functions (PDFs), which the log-likelihood function separates into sums, as shown in Equation (1) above. In the embodiment of a La-Ti solution, $Q_i$=Q and the relative weighting of Laplacian and Tikhonov is defined as $\tau$ and $1-\tau$, respectively where $0<\tau<1$. Adding the weighting parameter T to the quadratic cost function shown in Equation (1) with the La-Ti terms described above and differentiating the quadratic cost function with respect to $v_e$ results in Equation (3) below. It is linear in the unknown $v_e$ and thus the global best solution (according to a La-Ti scheme) may be obtained (without resorting to iteration) by linear algebra by solving Equation (3) below:

$$v_e^* = B_{La\text{-}Ti}v_p = [A^TA + \tau\lambda_i^2 L^TQL + (1-\tau)\lambda_i^2 Q]^{-1}A^Tv_p \quad (3)$$

where the superscript T again indicates the transpose of the underlying matrix, T is a weighting parameter as described above, and B is the BEM inverse transfer matrix that maps the measured voltages at electrodes 32 onto the endocardial voltage distribution, such that $Bv_p \rightarrow v_e$ (i.e., B is the regularized inverse of A). A larger $\tau$ in Equation (3) results in more weight for Laplacian regularization, and lower $\tau$ results in more weight for Tikhonov regularization. In an embodiment, a relatively high $\tau$ may yield a solution that adequately penalizes outlying measurements with Tikhonov regularization while providing a highly smoothed solution.

Equation (3) represents an exemplary embodiment of the La-Ti regularization scheme. As noted above, in embodiments, and as an alternative to Equation (3), different Q matrices may be used for the Laplacian and Tikhonov portions of a La-Ti regularization scheme (i.e., such that $Q_1 \neq Q_2$).

Once values are chosen for P, $Q_i$, N, $L_i$, and $b_i$, the method 64 may further includes a solution step 68 that includes determining the voltage distribution on the endocardial surface according to the collected voltages and the introduced Laplacian operator and Tikhonov regularization matrix by solving the error minimization formulation. As part of the solution step, and as noted above, Equation (3) (or another equation including a Laplacian operator and a Tikhonov regularization matrix, e.g., where $Q_1$ and $Q_2$ are the same or different) may be solved. Software and methods for finding a solution are known in the art and may be included in the ECU 12 (e.g., stored in the memory 40 and executed by the processor 42).

As noted above, the discretization step 55, formulation step 56, introduction step 66, and solution step 68 may be performed for a number of cardiac models associated with a number of different time portions of a cardiac cycle. The electrical behavior of a heart may thus be determined for all relevant portions of a heart cycle, in an embodiment. Once determined, the voltage distribution for one or more portions of a heart cycle may be used to create an activation map and/or other known representations of cardiac activity. Such representations may be displayed on or with a model of the heart.

Selecting Values for $Q_i$, N, $L_i$, $\lambda_1$, and $b_i$—Confidence Power Regularization.

Figure 6:
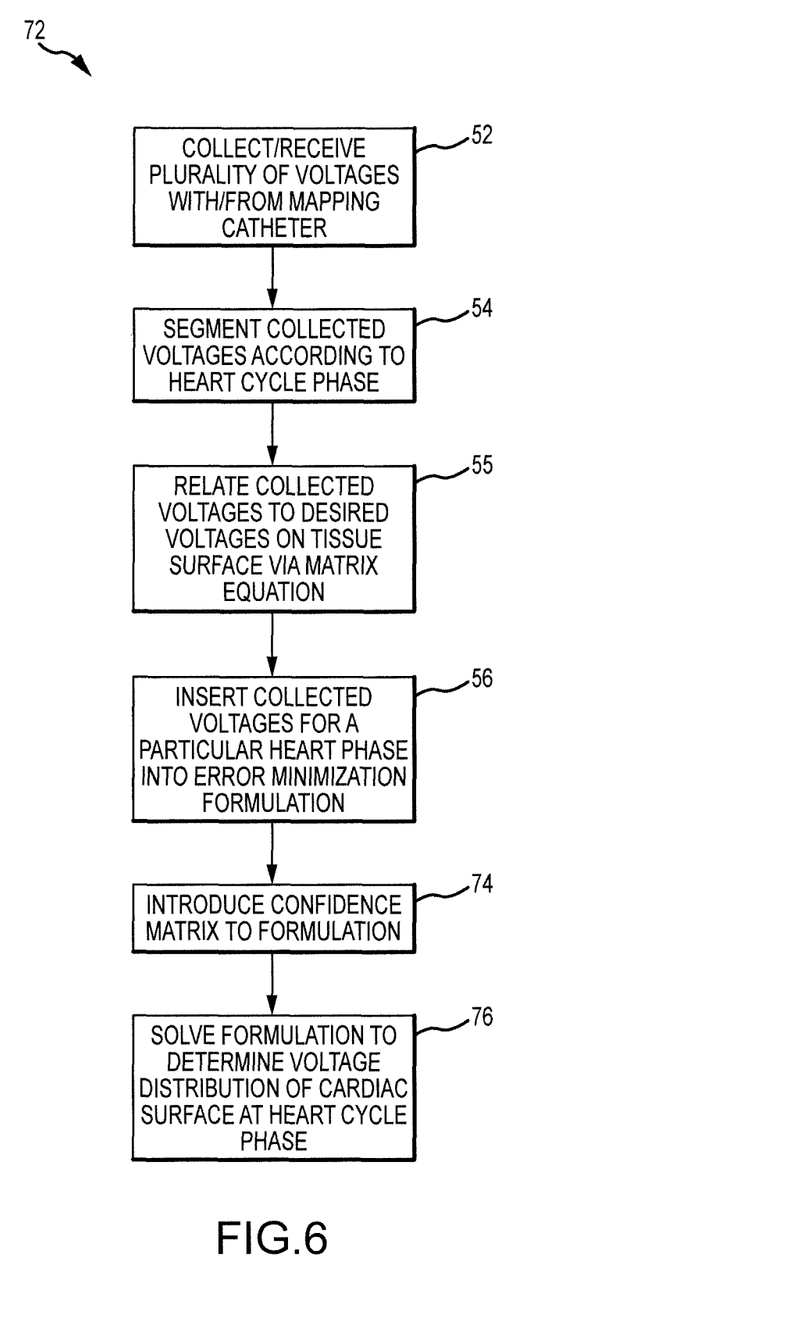
FIG. 6 is a flow chart depicting an exemplary method of determining a voltage distribution on the surface of the heart.

FIG. 6 is a flow chart depicting an exemplary method 72 of determining a voltage distribution on the surface of the heart. The method 72 illustrated in FIG. 6 is a specific embodiment of the method 50 illustrated in FIG. 4. The method 72 illustrated in FIG. 6 employs a "Confidence Power" regularization scheme, which may regularize based on some measure of "confidence" (i.e., based on probability of measurement accuracy, of likelihood of a high or low voltage, or another metric) in a regularization term at one or more (in some embodiments, every) points on the cardiac surface.

The method 72 may begin, like the broader method 50, with a voltage collection step 52, a segmentation step 54, a discretization step 55, and a formulation step 56, which may be performed as described above with respect to the broader method 50. The method 72 may further include an introduction step 74 that includes introducing to the error minimization formulation a confidence matrix, as explained below.

"Confidence" may be reflected in one or more of the matrices $Q_i$. As discussed above, values of $Q_i$ may be selected for use with Tikhonov regularization, in embodiments, to suppress voltages in regions of the endocardium known to be valves or vein ostia, where voltage is expected to be low (and, thus, where there is high confidence in low voltage). Similarly, in a Confidence Power scheme, values of $Q_i$ may be selected based on a known likelihood that the voltage distribution for one or more portions of the endocardium will have high or low voltage values. Thus, $Q_i$ may suppress values in the voltage distribution solution for portions of the endocardium known to have low voltage, and allow higher voltages in the voltage distribution scheme for portions of the endocardium known to have high voltage.

Alternatively, or in addition, confidence reflected in $Q_i$ may be based on the distance from an endocardial surface (e.g., a given node or other feature on a BEM or other anatomical model) to the nearest electrode on the measurement device. The closer an electrode is to the tissue, the higher the probability may be that the voltage detected by the electrode accurately measures a portion of the voltage distribution on the endocardium surface. In an embodiment, confidence may determine how strongly regularization is applied at each endocardial node j. For a distance-based confidence regularization term i, the diagonal elements of $Q_i$ may be set to $d_{jm}^{-\beta}$, where $d_{jm}$ is the distance from endocardial surface node j to the nearest measurement electrode m, and $\beta$ is a measure of confidence. In an embodiment, $\beta$ for a given $d_{jm}$ may be a value between zero (0) and (1). The larger the distance (and, accordingly, the lower the confidence) is, the stronger the regularization may be.

In the exemplary embodiment, a Confidence Power scheme may be applied to Tikhonov regularization with $N=1$, $L_1=I$, $b_1=0$, and $Q_1=Q$. Such an embodiment may also be conceptualized as an embodiment of La-Ti (i.e., as embodied in Equation (3) above) with $\tau=0$ and a specific Q (i.e., where Q is a confidence matrix). After introduction of such regularization terms to Equation (1) and differentiation over $v_e$, Equation (4) results:

$$v_e^* = B_{Tikhonov-ConfidencePower} v_p = [A^T A + \lambda_1^2 Q]^{-1} A^T v_p \quad (4)$$

Q may be a full positive semidefinite matrix (e.g., an inverse covariance matrix) or a diagonal matrix, in embodiments. As noted above, diagonal elements of Q may be selected based on a distance-based confidence. However, if Q is more complex than the identity matrix, Equation (4) may be less efficient to implement by software in a subsequent solution step of method 72.

In addition to or instead of $Q_i$, confidence may be reflected in the BEM forward transfer matrix A and its regularized inverse B as follows. First, confidence maybe low at an endocardial surface location j with corresponding voltage $v_e^j$ if $v_e^j$ can change with little to no effect on the observed probe voltages $v_p$ (i.e., because $v_e^j$ and $v_p$ are nearly uncorrelated through the forward transfer matrix A, where $v_p = A v_e + e_p$.). For such a location j, confidence may be proportional to the norm of column j of the matrix A. Second, as noted above and as shown in Equations (3) and (4), $v_e^* = B v_p$. Thus, small noise or uncertainty in the probe voltages $v_p$ translates to changes in $v_e^j$ proportional to the row norm of B. In an embodiment, endocardial surface locations j corresponding to rows of B with large norms may be assigned lower confidence values.

Another way of computing and/or visualizing a measure of confidence is based on a principal components analysis of the forward transfer matrix A. Using the singular value decomposition (SVD), the matrix A can be represented as $A = U \Sigma V^T$, where U and V are orthonormal matrices and E is a diagonal matrix of singular values. The columns of the matrix V represent the principal components of the inverse $v_p \rightarrow v_e$, so that any solution of the unregularized inverse problem (i.e., of the voltage distribution) can be represented as linear combination of these vectors (principal components). The principal components corresponding to the non-zero singular values, referred to below as the relevant principal components, may be used for constructing the solution to the inverse problem. In an embodiment, the number of relevant principal components may be equal to the number of electrodes used to collect the voltages in $v_p$ (e.g., the number of electrodes 32 on the basket assembly 30 of the mapping catheter 24). The areas of the endocardium on which the relevant principal components are capable of constructing a solution to the inverse are related to the areas of the endocardium onto which the relevant principal components map. To that end, for each point on the endocardial surface, a measure of confidence can be determined based on all relevant principal components. The confidence measure (e.g., for a plurality of points or all points on the endocardium) may be encoded as a value for color, hue, saturation, value, or transparency (or otherwise configured for display) and displayed on a model of the endocardium surface to represent an overall measure of confidence in the likelihood of a meaningful inverse solution for a given position of the mapping catheter. One such calculation of the confidence measure for each point on the surface can be based on the maximum absolute value of all relevant principal components at that point on the endocardium. The resulting confidence map depends on the transfer matrix A, which in turn depends on the locations of the electrodes used to collect the voltages in $v_p$. A confidence map could be updated in real time to provide visual feedback to the user and enable the optimal placement of the mapping catheter to maximize confidence.

A confidence map as described above may thus provide, instead of just best estimates of endocardial voltage, visual feedback of confidence in those estimates. Such a confidence map may be a useful guide for placing a noncontact mapping catheter to obtain good voltages at specific locations in the heart. Such a confidence map (or the data underlying such a map, i.e., the relevant principal components described above) may be used by a system to mask maps or discard data based on myocardial voltage estimates from locations with little confidence—i.e., timing and/or voltage data may be used and/or displayed only if obtained when the non-contact mapping catheter is in an area or position with confidence above a selected threshold.

Figure 7:
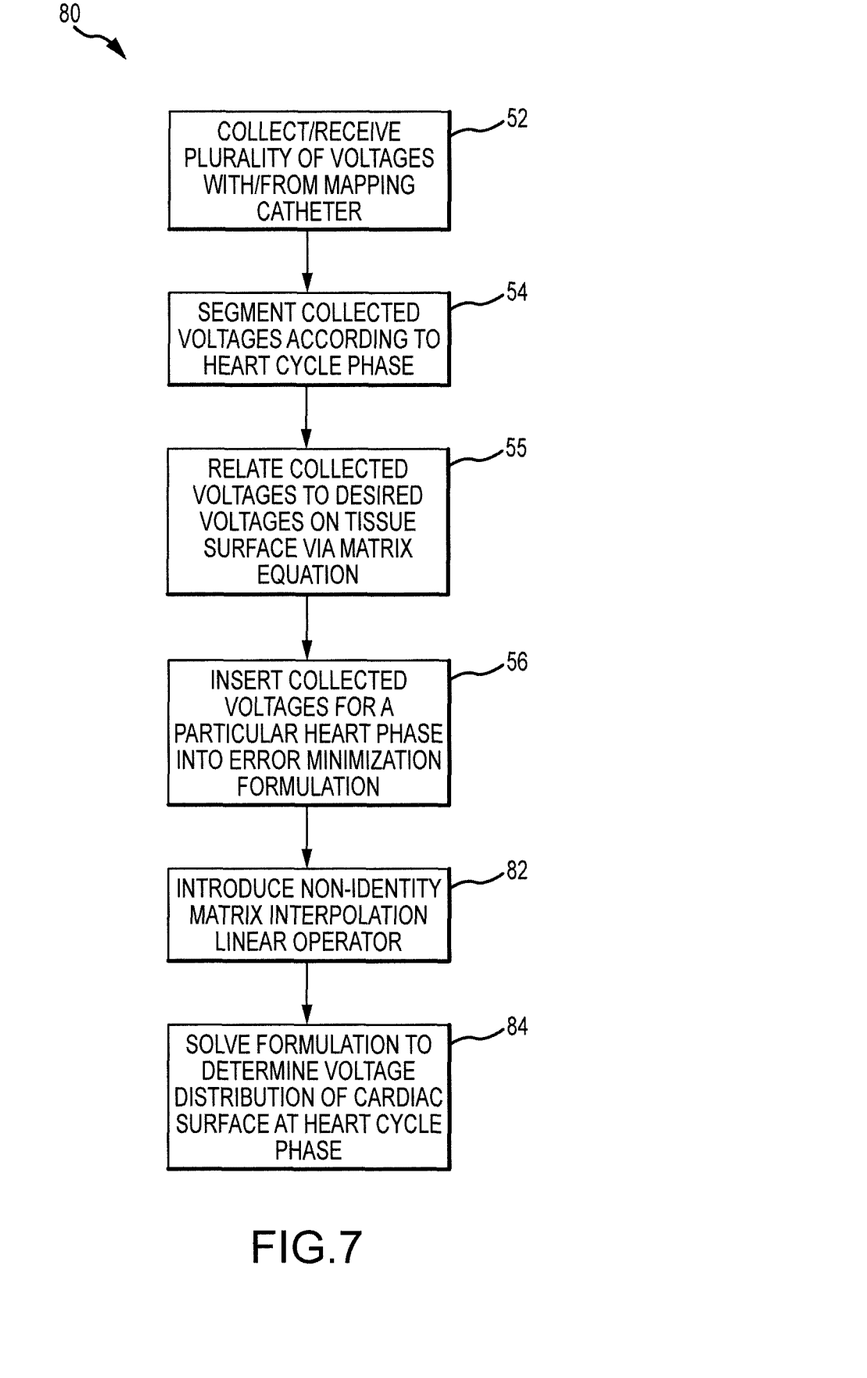
FIG. 7 is a flow chart depicting an exemplary method of determining a voltage distribution on the surface of the heart.

The Confidence Power algorithm can be applied in conjunction with other types of regularization, including Tikhonov, Laplacian, La-Ti, vProbe (discussed below), and others not discussed in detail in this disclosure. For example, as noted above, Confidence Power can be combined with La-Ti by altering the values of $Q_1$ and/or $Q_2$ in a version of Equation (3).

Once values are chosen for P, $Q_i$, N, $L_i$, $\lambda_i$, and $b_i$, according to the Confidence Power technique (e.g., in conjunction with one or more other regularization schemes), the method 72 may further include a solution step 76 that includes determining the voltage distribution on the endocardial surface according to the collected voltages and the introduced confidence matrix by solving the error minimization formulation. As part of the solution step 76 and as noted above, Equation (4) (or another equation including a confidence matrix) may be solved. Software and methods for finding a solution are known in the art and may be included in the ECU 12 e.g., stored in the memory 40 and executed by the processor 42).

As noted above, the discretization step 55, formulation step 56, introduction step 74, and solution step 76 may be performed for a number of cardiac models associated with a number of different time portions of a cardiac cycle. The electrical behavior of a heart may thus be determined for all relevant portions of a heart cycle, in an embodiment. Once determined, the voltage distribution for one or more portions of a heart cycle may be used to create an activation map and/or other known representations of cardiac activity. Such representations may be displayed on or with a model of the heart.

Selecting Values for $Q_i$, N, $L_i$, $\lambda_i$, and $b_i$—vProbe Regularization.

FIG. 7 is a flow chart depicting a method 80 of determining a voltage distribution on the surface of the heart. The method 80 illustrated in FIG. 7 is a specific embodiment of the method 50 illustrated in FIG. 4. The method 80 illustrated in FIG. 7 includes the "vProbe" regularization scheme.

The method 80 may begin, like the broader method 50, with a voltage collection step 52, a segmentation step 54, a discretization step 55, and a formulation step 56, which may be performed as described above with respect to the broader method 50. The method 80 may continue to an introduction step 82 that includes introducing to the error minimization formulation a linear operator that interpolates the measured voltages to the voltage distribution, as explained below.

In an embodiment of vProbe regularization, $\lambda^2 \|v_e - Mv_p\|^2$ may be used as a regularization term, for some linear operator M that interpolates or extrapolates the electrode voltages $v_p$ to the points on the cardiac tissue surface. Accordingly, in an embodiment of vProbe regularization, $N=1$, $L_1=I$, $Q_i=Q$, $\lambda_1=\lambda$, and $b_i=Mv_p$. M may be selected from, for example and without limitation, Radial Basis Functions (RBFs), Mean Value Coordinates, or Thin Plate Splines. Another way of conceptualizing vProbe is that the reconstructed endocardial voltages $v_e$ are biased toward some function of the observed voltages $v_p$. If the voltages in $v_p$ are higher on one side or in one region of the catheter than the rest, the values of the endocardial voltage distribution $v_e$ will be biased higher in a portion of the endocardium associated with that side or region (and, conversely, biased lower in a portion of the endocardium associated with a side or region of the catheter measuring lower voltages).

As noted above, in an embodiment, RBFs may be used for vProbe. Examples of basis functions that may be used in RBFs in a vProbe regularization include, but are not limited to $\exp(-cr^2)$, $r^2 \log r$, $|r|$, and $1/r$. Using a chosen basis function, the matrix M may be constructed using techniques known in the art, so that $Mv_p$ interpolates/extrapolates the electrode voltages $v_p$ to a voltage field at each node of the endocardial model, the voltage distribution of which model is represented by $v_e$.

Introducing the vProbe regularization terms noted above into the generalized Equation (1) and differentiating over $v_e$ gives the exemplary vProbe solution shown in Equation (5) below:

$$v_e^* = B_{vProbe} v_p = (A^T A + \lambda^2 Q)^{-1}(A^T A + \lambda^2 QM) v_p \qquad (5)$$

Once values are chosen for P, $Q_i$, N, $L_i$, $\lambda_i$, and $b_i$, the method 80 may further include a solution step 84 that includes solving the error minimization formulation, including the introduced linear operator M, to determine the voltage distribution on the endocardial surface. As part of the solution step, and as noted above, Equation (5) (or another equation including a linear operator (i.e., M) that interpolates the collected voltages $v_p$ to the endocardial surface voltage distribution $v_e$) may be solved. Software and methods for finding a solution are known in the art and may be included in the ECU 12 (e.g., stored in the memory 40 and executed by the processor 42.

As noted above, the discretization step 55, formulation step 56, introduction step 82 and solution step 84 may be performed for a number of cardiac models associated with a number of different time portions of a cardiac cycle. The electrical behavior of a heart may thus be determined for all relevant portions of a heart cycle, in an embodiment. Once determined, the voltage distribution for one or more portions of a heart cycle may be used to create an activation map and/or other known representations of cardiac activity. Such representations may be displayed on or with a model of the heart.

Although a number of embodiments have been described above with a certain degree of particularity, those skilled in the art could make numerous alterations to the disclosed embodiments without departing from the sprit or scope of this disclosure. For example, all joinder referenced (e.g., attached, coupled, connected, and the like) are to be construed broadly and may include intermediate members between a connection of elements and relative movement between elements. As such, joined references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by referenced herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for determining a voltage distribution on a surface of a cardiac tissue, comprising:
   transforming a received plurality of voltages collected by a plurality of electrodes adjacent to the surface into a digital representation of the plurality of voltages, with a computer;
   introducing a first and second regularization term to an error minimization formulation associated with the digital representation of the plurality of voltages;
   determining, by a processor associated with the computer, the voltage distribution according to said plurality of voltages and according to said regularization terms of the error minimization formulation;
   wherein the first of said regularization terms comprises a Laplacian smoothness operator and the second of said regularization terms comprises a Tikhonov regularization matrix;
   increasing a weight of one of the first and second regularization terms while decreasing a weight of the other one of the first and second regularization terms, wherein the weights of the first and second regularization terms each include a weighting parameter, and wherein the weighting parameter of the first regularization term is defined as $\tau$ and the weighting parameter of the second regularization term is defined as $1-\tau$, where $\tau$ is greater than zero and less than one; introducing to the error minimization formulation a confidence matrix, wherein a term of said confidence matrix is associated with at least one of a known first confidence that one or more of said plurality of voltages accurately measures a portion of said voltage distribution and a known second confidence that a portion of said voltage distribution exceeds a threshold and wherein the confidence matrix includes terms set to zero, the terms corresponding to one or more of said electrodes that are inoperable; and
   displaying a portion of the voltage distribution on a model of the cardiac tissue.

2. The method of claim 1, further comprising constructing a matrix expression relating the desired voltages on the surface of the cardiac tissue to the plurality of voltages.

3. The method of claim 2, wherein the matrix expression is constructed using a Finite Element Method (FEM) or a Boundary Element Method (BEM).

4. The method of claim 1, wherein said first confidence is associated with a known distance between one or more of said plurality of electrodes and one or more portions of said cardiac tissue.

5. The method of claim 1, wherein a first confidence term is applied to the first regularization term and a second confidence term is applied to the second regularization term, and wherein the first and second confidence terms are representative of a distance between the surface of the cardiac tissue and a nearest one of the plurality of electrodes.

6. The method of claim 5, wherein a confidence associated with the first confidence term and the second confidence term increases as the distance between the surface of the cardiac tissue and the nearest one of the plurality of electrodes decreases.

7. The method of claim 6, wherein:
   the first confidence term and the second confidence term are matrices; and
   diagonal terms of the matrices are set to the formula $d_{jm}^{-\beta}$, where $d_{jm}$ is a distance between the surface of the cardiac tissue j and the nearest one of the plurality of electrodes m and $\beta$ is a measure of confidence.

8. A method for determining a voltage distribution on a surface of a cardiac tissue, comprising:
   transforming a received plurality of voltages collected by a plurality of electrodes adjacent to the surface into a digital representation of the plurality of voltages, with a computer;
   introducing a first and second regularization term to an error minimization formulation associated with the digital representation of the plurality of voltages;
   determining, by a processor associated with the computer, the voltage distribution according to said plurality of voltages and according to said regularization terms of the error minimization formulation;
   wherein one of said regularization terms comprises a linear operator that interpolates said plurality of voltages to said voltage distribution, wherein said linear operator is other than an identity matrix;
   increasing a weight of one of the first and second regularization terms and decreasing a weight of the other one of the first and second regularization terms at a same time, wherein the weight of the first regularization term is defined as $\tau$ and the weight of the second regularization term is defined as $1-\tau$, where $\tau$ is greater than zero and less than one, wherein a first confidence matrix is applied to the first regularization term and a second confidence matrix is applied to the second regularization term, and wherein the first and second confidence matrices are representative of a distance between the surface of the cardiac tissue and a nearest one of the plurality of electrodes, wherein a term of at least one of the first and second confidence matrices is associated with at least one of a known first confidence that one or more of said plurality of voltages accurately measures a portion of said voltage distribution and a known second confidence that a portion of said voltage distribution exceeds a threshold and wherein the confidence matrices include terms set to zero, the terms corresponding to one or more of said electrodes that are inoperable; and
   displaying a portion of the voltage distribution on a model of the cardiac tissue.

9. The method of claim 8, wherein said linear operator uses a radial basis function.

10. The method of claim 9, wherein said radial basis function is one of $\exp(-cr^2)$, $r^2 \log r$, $|r|$, and $1/r$.

11. The method of claim 8, wherein said linear operator uses mean value coordinates.

12. The method of claim 9, wherein said linear operator uses thin plate splines.

13. The method of claim 9, wherein a third of said regularization terms includes values derived from a known solution to a portion of said voltage distribution, further wherein said linear operator relates said plurality of voltages to the dimensions of said another of said regularization terms.

\* \* \* \* \*